United States Patent [19]
Williams et al.

[11] Patent Number: 5,814,303
[45] Date of Patent: Sep. 29, 1998

[54] DENTAL PRODUCT

[75] Inventors: David Robert Williams, Monroe; Stephen Roy Barrow, Trumbull, both of Conn.

[73] Assignee: Chesebrough-Pond's USA Co., Division of Conocpo, Inc., Greenwich, Conn.

[21] Appl. No.: 932,412

[22] Filed: Sep. 17, 1997

[51] Int. Cl.⁶ .............................. A61K 7/16; A61K 7/18; A61K 7/20
[52] U.S. Cl. ................. 424/57; 414/49; 414/52; 414/53
[58] Field of Search .......................... 424/49–88

[56] References Cited

U.S. PATENT DOCUMENTS

| | | |
|---|---|---|
| 4,528,180 | 7/1985 | Schaeffer . |
| 4,627,977 | 12/1986 | Gaffar et al. . |
| 4,687,663 | 8/1987 | Schaeffer . |
| 4,849,213 | 7/1989 | Schaeffer . |
| 4,895,721 | 1/1990 | Drucker ................................. 424/53 |
| 5,020,694 | 6/1991 | Pettengill . |
| 5,038,963 | 8/1991 | Pettengill et al. . |
| 5,260,062 | 11/1993 | Gaffar ................................... 424/401 |
| 5,302,374 | 4/1994 | Wagner ................................... 424/52 |
| 5,335,827 | 8/1994 | Gentile . |
| 5,565,190 | 10/1996 | Santalucia et al. ..................... 424/53 |
| 5,597,554 | 1/1997 | Wagner ................................... 424/53 |
| 5,599,525 | 2/1997 | Hsu et al. ............................... 424/59 |
| 5,599,527 | 2/1997 | Hsu et al. ............................... 424/52 |
| 5,614,174 | 3/1997 | Hsu et al. ............................... 424/53 |
| 5,676,933 | 10/1997 | Hauschilo ............................... 424/53 |
| 5,683,680 | 11/1997 | Santalucia et al. ..................... 424/53 |
| 5,690,913 | 11/1997 | Hsu et al. ............................... 424/53 |
| 5,698,182 | 12/1997 | Prencipe et al. ....................... 424/53 |

FOREIGN PATENT DOCUMENTS

97/46462  12/1997  WIPO .

*Primary Examiner*—Shep K. Rose
*Attorney, Agent, or Firm*—Milton L. Honig

[57] ABSTRACT

A dental product is provided packaged in a telescopically arranged multi-cavity dispensing container having at least two cylinders in an upper body thereof. Peroxide and baking soda are placed as active ingredients in separate respective semi-solid streams, each stream being in separate ones of the cylinders. Uniform dispensing of each stream to deliver relatively equivalent ribbon length of each stream by incorporating a polyphosphate salt to adjust viscosity. Preferred salts are tripolyphosphates, hexametaphosphates and pyrophosphates.

6 Claims, 1 Drawing Sheet

FIG.
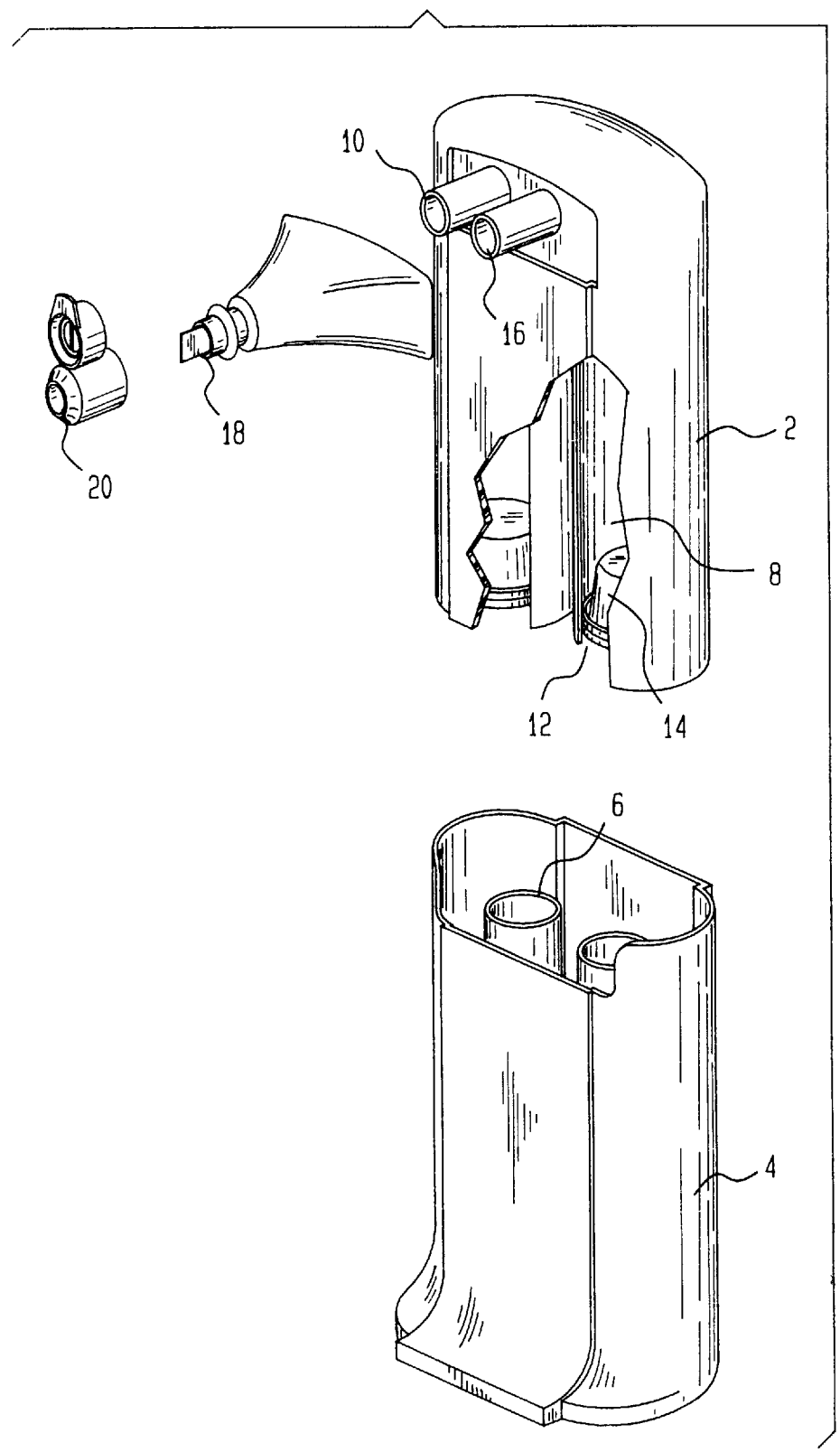

DENTAL PRODUCT

BACKGROUND OF THE INVENTION

1. Field of the Invention

The invention relates to a dental product, more particularly a telescopically arranged multi-cavity dispensing container two of which cavities are filled with semi-solid dentifrice compositions respectively containing peroxide and baking soda as active ingredients.

2. The Related Art

Oral compositions with peroxide and baking soda (i.e. sodium bicarbonate) have become commercially quite popular. The combination of actives has been reported to promote healthy gums. When in contact, peroxide and baking soda are reactive towards one another. Therefore these ingredients must be maintained separately until time of use. Dispensing packages have been developed which physically isolate peroxide and baking soda by separating them into different compartments. This approach has been described in a series of patents to Schaeffer including U.S. Pat. No. 4,849,213, U.S. Pat. No. 4,528,180 and U.S. Pat. No. 4,687,663.

Dosing of flavor, fluoride and other actives has always been a challenge from multi-compartment dispensers that simultaneously extrude more than one stream of toothpaste. Unequal dispensing may adversely effect taste, aesthetics and oral hygiene. The most successful package for controlled delivery has been a telescopically arranged multi-cavity dispensing pump, especially as described in U.S. Pat. No. 5,020,694 and U.S. Pat. No. 5,038,963 and U.S. Pat. No. 5,335,827 (relating to a refill cartridge), all of which are herein incorporated by reference. Commercially the pump is embodied in Mentadent® Peroxide and Baking Soda toothpaste.

Consumers have noted that even with telescoping pumps it is often difficult to extrude equal lengths of respective peroxide and baking soda dentifrice ribbons.

Accordingly, it is an object of the present invention to provide a peroxide and baking soda dental product based on a telescopically arranged multi-cavity dispensing container wherein essentially identical toothpaste ribbons from each of the cavities can be dispensed.

Another object of the present invention is to provide a peroxide and baking soda dental product packaged in a telescopically arranged multi-cavity dispensing container wherein viscosity of each cavity stream can be better controlled thereby allowing more accurate dosing.

These and other objects of the present invention will become more readily apparent from consideration of the following summary and detailed discussion.

SUMMARY OF THE INVENTION

A dental product is provided including:

(i) a dispensing container with an upper and a lower body which are telescopially engageable one with another, the upper body including at least two hollow and separate cylinders, the cylinders having a first generally closed end and a second end telescopically and slidingly accommodating at least two parallel pistons which conform to ride sealingly along the interior walls of the cylinders so as to force any flowable materials to flow toward the first end of the cylinder upon relative compression of the cylinders and pistons, the cylinders having outlet channels;

(ii) an outlet means in fluid communication with the outlet channels, the outlet means including adjacent outlet openings unconnected to each other and having means for causing the flowable materials to flow toward each other at the outlet openings to form a single, banded, unmixed stream;

(iii) a first semi-solid flowable material containing a peroxide and a second semi-solid flowable material containing a bicarbonate salt, each of the first and second semi-solid materials otherwise having unmatched flow properties and being stored in separate ones of the at least two hollow parallel cylinders, at least one of the semi-solid materials containing from 0.05 to 20% of a polyphosphate effective to equalize the actuation forces, and to control viscosity of each semi-solid and to thereby achieve closer uniformity of extrusion between the two separate semi-solids.

BRIEF DESCRIPTION OF THE DRAWING

The above features, advantages and objects of the present invention will more fully be appreciated through the following detailed discussion, reference being made to the drawing consisting of a single Figure which is an expanded view of a telescopically arranged multi-cavity dispensing pump.

DETAILED DISCUSSION

Now it has been found that in the context of telescopically arranged multi-cavity dispensing pumps, control of the flowable toothpaste contents can be obtained through use of polyphosphates in the formulation. Polyphosphates allow for close matching of flow properties between a peroxide and a baking soda active containing stream. Flavors, fluoride and actives formulated in either or both of the flowable streams, can therefore be dosage regulated with high accuracy. Both streams can be extruded with much better control.

The dispensing container of the present invention as shown in the Figure includes an upper body 2 and a lower 4, the former telescopically engaging within the latter. Within the lower body 4 are a pair of parallel piston rods 6 rigidly standing, and preferably unitarily molded with the lower body. These rods may be hollow or solid. While the depicted configuration is round, the rods may be rectangular or of any other polygonal shape.

Upper body 2 includes a pair of separate parallel cylinders 8 each having a first generally closed end 10 and a second end 12 telescopically and slidingly accommodating piston heads 14. These heads conform to ride sealingly along interior walls of the cylinders so as to force flowable materials to flow towards the first end of the cylinder. The cylinder walls may be formed as part of the upper body or may be formed as refill cartridges separate and removable from the upper body. Activation of flow is accomplished by hand pressure downward on the top of the upper body which pressure forces the upper body to telescopically descend within the lower body. Movement of the bodies causes pistons 6 against each of the respective piston heads 14 to move upward along respective cylinders 8. Flowable material in each of the cylinders is then forced through a pair of outlet channels 16. Flowable toothpaste exits the outlet channels passing in unmixed streams through an outlet nozzle having a septum 18 maintaining respective toothpastes in unmixed relationship to outlet openings 20.

First and second semi-solid extrudable streams of dentifrice will be stored in each of the respective cylinders 8. The first of the streams will include a peroxide component such as an alkali metal perborate, percarbonate, urea peroxide, persilicate, perphosphate, calcium peroxide or hydrogen peroxide. Most suitable for this invention is hydrogen peroxide. Amounts of the peroxide may range from 0.01 to 15%, preferably from 0.5 to 3% by weight of the first material.

The peroxide containing composition may either be a paste or gel, preferably the latter. When a gel, water will be present in amounts ranging from 20 to 70%, preferably from 30 to 55%, optimally between 30 to 40% by weight of the first material.

For anti-caries protection, a source of fluoride ion will normally be present in one or both of the flowable materials of the total oral composition. Fluoride sources include sodium fluoride, potassium fluoride, calcium fluoride, stannous fluoride, stannous monofluorophosphate and sodium monofluorophosphate. These sources should release anywhere from 25 to 3500 ppm of fluoride ion. The anti-caries agent will be present in an amount from about 0.05 to about 3% by weight, preferably 0.2 to 0.6% by weight of the total oral composition.

Essential for the present invention are polyphosphate salts. Most suitable are the hexametaphosphates, tripolyphosphates and pyrophosphates. Counterions for these phosphates may be the alkali metal, alkaline earth metal, ammonium, $C_2$–$C_6$ alkanolammonium and salt mixtures thereof. Representative of polyphosphates are sodium tripolyphosphate, sodium hexametaphosphate, potassium hydrogen phosphate, sodium hydrogen phosphate, disodium pyrophosphate, dipotassium pyrophosphate, tetrasodium pyrophosphate, tetrapotassium pyrophosphate and mixtures of these salts. Amounts of the polyphosphate may range from 0.5 to 20%, preferably from 1 to 8%, optimally from 1.2 to 4.5% by weight of the respective stream.

Viscosity as measured on a Brookfield RVT, E Bar 2.5 RPM, for each of the semi-solid material streams may range from 20,000 to 1,500,000 centipoise, preferably from 50,000 to 800,000 centipoise at 25° C.

A variety of other ingredients normally present in dentifrices can be selected for the semi-solid streams of peroxide and bicarbonate of the present invention. When the semi-solid is a gel, it is usual to employ a thickening agent with the water that is a cross-linked acrylic polymer. Alternatively and most preferably gels can be structured with a polyoxyethylene-polyoxypropylene copolymer. Commercially, the copolymers are available from the BASF Corporation under the trademark Pluronic F88, F99, F108 and F117. Most preferred is Pluronic F127 (more commonly described by its CTFA name, Poloxamer 407) which has a molecular weight ranging from 10,000 to 15,000, and containing 70% of the hydrophilic polyoxyethylene moiety. Amounts of the copolymer can range anywhere from 18–25% by weight, preferably between 19 and 24%. Poloxamers are particularly suitable for this invention because of their wide pH tolerance, high compatibility with hydrogen peroxide and unique gel properties.

Advantageously, glycerol should also be present in the gel component in an amount from 15 to 60%, preferably in an amount greater than 30% but less than 50%, optimally between 35 to 45% by weight of the gel component.

A low pH, preferably a pH no higher than 4, optimally less than 3.3, should be maintained for the gel component. Acidification is best accomplished through use of a phosphorus-based inorganic or organic acid. Where Carbomer is used as a gel structurant, pH can be as high as 7.5.

The second component of the oral compositions of the invention will preferably be a bicarbonate-containing opaque paste. Elements of this component are outlined below.

Advantageously, the bicarbonate will be the salt of an alkali metal such as sodium or potassium. Normally, the bicarbonate is included in the composition in an amount sufficient to provide a neutral or basic pH when the composition is contacted with water, preferably a pH of from 7.0 to 9.5, most preferably 8.0 to 9.0. Typically, the concentration will range from 0.5 to 80%, preferably from 5 to 50%, optimally between 8 and 20% by weight of the second semi-solid material.

A humectant and water system will normally be included. Humectants are usually polyols which, for example, may include glycerol, sorbitol, propylene glycol, lactitol, xylitol, polypropylene glycol, polyethylene glycol, hydrogenated corn syrup and mixtures thereof. Generally the amount of humectant will range from 25 to 90%, preferably from 40 to 70% by weight of the first or second semi-solid material. Particularly preferred is a liquid mixture of 3 to 30% water, 0 to 80% glycerol and/or 20 to 80% sorbitol.

A natural or synthetic thickening agent may be present in an amount from 0.1 to 10%, preferably 0.5 to 5% by weight of the second semi-solid material may be present. Thickeners may include hydroxypropyl methylcellulose, hydroxyethyl cellulose, sodium carboxymethyl cellulose, xanthan gum, tragacanth gum, karaya gum, arabic gums, Irish moss, starch, alginates and carrageenans.

Surfactants are normally also included in the semi-solid materials, especially the second component of the oral compositions of this invention. These surfactants may be of the anionic, nonionic, cationic or amphoteric type. Most preferred are sodium lauryl sulfate, sodium dodecylbenzene sulfonate and sodium laurylsarcosinate. Surfactants are usually present in an amount from 0.5 to 5% by weight of a respective semi-solid component.

An abrasive in addition to the bicarbonate will normally be included in the second component paste. Abrasives may be selected from water-insoluble alkali or alkaline earth metal salts of carbonate, aluminate and silicate. Especially preferred are silica, and alumina. Amounts of the abrasive will range from 5 to 80% by weight of a respective semi-solid component.

Sweetening agents such as saccharin, sodium cyclamate, aspartame, sucrose and the like may be included at levels from 0.1 to 5% by weight of a respective semi-solid component.

Other additives may also be incorporated into the oral compositions including preservatives, silicones, other synthetic or natural polymers such as Gantrez S-97, and antigingivitis actives.

The following examples will more fully illustrate the embodiments of this invention. All parts, percentages and proportions referred to herein and in the appended claims are by weight of the total composition unless otherwise stated.

EXAMPLE 1

Typical of the present invention are paste and gel components whose formulations are detailed under Tables I and II.

TABLE I

Bicarbonate Paste Component

| INGREDIENT | WT. % |
|---|---|
| Polyol II (sorbitol and other sugars) | 48.70 |
| Syloid 63XX (abrasive silica) | 15.00 |
| Sodium Bicarbonate | 10.00 |

TABLE I-continued

Bicarbonate Paste Component

| INGREDIENT | WT. % |
|---|---|
| PEG 32 (polyethylene glycol) | 5.00 |
| Sylox 15x (thickening silica) | 4.60 |
| Flavor | 1.00 |
| Tetrasodium Pyrophosphate | 0.50 |
| Sodium Lauryl Sulfate | 2.98 |
| SD Alcohol 38B | 2.85 |
| Cellulose Gum | 0.80 |
| Sodium Saccharin | 4.00 |
| Sodium Fluoride | 0.44 |
| Titanium Dioxide | 0.30 |
| Deionized Water | Balance |

TABLE II

Peroxide Gel Component

| COMPONENT | WT. % |
|---|---|
| Pluronic F127 | 20.00 |
| Glycerin | 20.00 |
| REG-600 | 10.00 |
| PEG 1450 | 10.00 |
| Hydrogen Peroxide (35% food grade) | 4.285 |
| FD&C Blue | 0.005 |
| Phosphoric Acid (85% w/w) | 0.15 |
| Deionized Water | Balance |

EXAMPLE 2

Another set of formulations suitable for the present invention are the paste and gel components detailed under Tables III and IV.

TABLE III

| COMPONENT | WT. % |
|---|---|
| Sorbitol | 49.11 |
| Syloid 63XX (abrasive silica) | 15.00 |
| Sodium Bicarbonate | 15.00 |
| PFG 32 (polyethylene glycol) | 5.00 |
| Sylox 15x (thickening silica) | 4.00 |
| Sodium Hexametaphosphate | 4.00 |
| Sodium Lauryl Sulfate | 2.98 |
| SD Alcohol 38B | 2.85 |
| Cellulose Gum | 0.80 |
| Sodium Saccharin | 0.50 |
| Sodium Fluoride | 0.46 |
| Titanium Dioxide | 0.30 |

TABLE IV

| COMPONENT | WT. % |
|---|---|
| Carbopol 940 (2% solution) | 20.00 |
| Glycerin | 40.00 |
| Hydrogen Peroxide | 4.30 |
| FD&C Blue | 0.005 |
| Sodium Hydroxide (50% soln) | adjusted to pH 7.0 |
| Deionized Water | Balance |

EXAMPLE 3

This example illustrates a paste and gel combination incorporating pyrophosphate in the gel, the formulations being detailed under Tables V and VI.

TABLE V

| INGREDIENT | WT. % |
|---|---|
| Polyol II (sorbitol and other sugars) | 48.71 |
| Sodium Bicarbonate | 20.00 |
| Calcium Carbonate | 15.00 |
| PEG 32 (polyethylene glycol) | 5.00 |
| Sodium Lauryl Sulfate | 3.00 |
| SD Alcohol 38B | 3.00 |
| Sodium Monofluorophosphate | 2.10 |
| Flavor | 1.00 |
| Cellulose Gum | 0.80 |
| Sodium Saccharin | 0.50 |
| Titanium Dioxide | 0.30 |
| Deionized Water | Balance |

TABLE VI

| COMPONENT | WT. % |
|---|---|
| Pluronic F127 | 25.00 |
| Glycerin | 25.00 |
| PEG 1450 | 10.00 |
| Hydrogen Peroxide (35% food grade) | 4.00 |
| Dipotassium Pyrophosphate | 0.750 |
| Disodium Pyrophosphate | 0.750 |
| FD&C Blue | 0.005 |
| Phosphoric Acid (85% w/w) | 0.10 |
| Deionized Water | Balance |

EXAMPLE 4

This example illustrates a paste and gel combination incorporating phosphates in both formulations as detailed under Tables VII and VIII.

TABLE VII

| INGREDIENT | WT. % |
|---|---|
| Sorbitol | 35.34 |
| Glycerin | 15.00 |
| Syloid 63XX (abrasive silica) | 15.00 |
| Sodium Bicarbonate | 15.00 |
| PEG 32 (polyethylene glycol) | 5.000 |
| Sylox 15x (thickening silica) | 4.60 |
| Sodium Lauryl Sulfate | 2.50 |
| SD Alcohol 38B | 2.50 |
| Sodium Hexametaphosphate | 2.00 |
| Cellulose Gum | 0.80 |
| Sodium Saccharin | 0.50 |
| Sodium Fluoride | 0.46 |
| Titanium Dioxide | 0.30 |
| Deionized Water | Balance |

TABLE VIII

| COMPONENT | WT. % |
|---|---|
| Pluronic F127 | 25.000 |
| Glycerin | 35.000 |
| Hydrogen Peroxide (35% food grade) | 10.00 |
| Tetrapotassium Pyrophosphate | 4.00 |
| FD&C Blue | 0.005 |
| Phosphoric Acid (85% w/w) | 0.10 |
| Deionized Water | Balance |

EXAMPLE 5

A series of experiments were conducted to establish the performance benefits of polyphosphates to achieve closer uniformity of extrusion between two separate dentifrice streams of a dual compartment dispensing container. Base formulas for each of these streams are set forth under Table IX and X respectively.

TABLE IX

| INGREDIENT | WEIGHT % |
|---|---|
| Polyol (sorbitol and other sugars) | 47.14 |
| Syloid 63XX | 15.00 |
| Sodium Bicarbonate | 10.00 |
| Deionized Water | 7.96 |
| REG 32 (polyethylene glycol) | 5.00 |
| Sylox 15X | 6.00 |
| Sodium Lauryl Sulfate | 2.98 |
| SD Alcohol 38B | 2.84 |
| Flavor | 1.30 |
| Menthol | 0.50 |
| Sodium Saccharin | 0.54 |
| Sodium Fluoride | 0.44 |
| Titanium Dioxide | 0.30 |

TABLE X

| INGREDIENT | WEIGHT % |
|---|---|
| Glycerin | 40.00 |
| Deionized Water | 35.56 |
| Hydrogen Peroxide | 4.285 |
| FD&C Blue | 0.005 |
| Phosphoric Acid | 0.15 |
| Pluronic F-127 | 20.00 |

Each of the dual compartments of dispensers of the type shown in the accompanying figure were separately charged with the formulations shown in Tables IX and X. Varying amounts and types of polyphosphates were then incorporated into either the peroxide or bicarbonate phase at the levels indicated in Table XI.

Streams of dentifrice from each of the Test formulas were placed into barrels of the dispenser shown in the Figure. Piston bottoms of these dispensers were then positioned against a stationary rod and placed within an Instron force measurement device. Actuation force necessary to extrude formula from the cylinder was then measured on the Instron equipment. Results are listed in Table XI.

TABLE XI

| COMPONENT | % Polyphosphate | ACTUATION FORCE IN Kg |
|---|---|---|
| Peroxide Phase | | |
| Control | 0 | 2.83 |
| Disodium Dihydrogen Pyrophosphate | 1 | 3.38 |
| Tetrasodium Pyrophosphate | 4 | 4.63 |
| Bicarbonate Phase | | |
| Control | 0 | 4.65 |

It can be seen that peroxide gel and bicarbonate paste phases can be provided with equalized actuation forces through proper formulation of pyrophosphate salts. For instance, a typical bicarbonate paste with 4.65 actuation force can be coupled with a 4% tetrapotassium pyrophosphate formulated gel. Absent the pyrophosphate, the gel phase would have an actuation force of 2.83. With such a low force, the peroxide gel would tend to dispense faster than the bicarbonate paste thereby causing difficulties for a consumer to dispense equal amounts of both ribbons.

The foregoing description and Examples illustrate selected embodiments of the present invention and in light thereof various modifications will be suggested to one skilled in the art, all of which are within the spirit and purview of this invention.

What is claimed is:

1. A dental product comprising:

(i) a dispensing container with an upper and a lower body which are telescopically engageable one with another, the upper body including at least two hollow and separate parallel cylinders, the cylinders having a first generally closed end and a second end telescopically and slidingly accommodating at least two parallel pistons which conform to ride sealingly along the interior walls of the cylinders so as to force any flowable materials to flow toward the first end of the cylinder upon relative compression of the cylinders and pistons, the cylinders having outlet channels;

(ii) an outlet means in fluid communication with the outlet channels, the outlet means including adjacent outlet openings unconnected to each other and having means for causing the flowable materials to flow toward each other at the outlet openings to form a single, banded, unmixed stream;

(iii) a first semi-solid flowable material containing a peroxide and second semi-solid flowable material containing a bicarbonate salt, each of the first and second semi-solid materials otherwise having unmatched flow properties and being stored in separate ones of the at least two hollow parallel cylinders, at least one of the semi-solid materials containing from 0.05 to 20% of a polyphosphate effective to equalize the actuation forces, and to control viscosity of each semi-solid and to thereby achieve closer uniformity of extrusion between the two separate semi-solids.

2. The dental product according to claim 1 wherein the polyphosphate is selected from the group consisting of tripolyphosphate, hexametaphosphate and pyrophosphate.

3. The dental product according to claim 2 wherein the pyrophosphate is an alkali metal salt selected from the group consisting of tetrasodium pyrophosphate, tetrapotassium pyrophosphate, dipotassium pyrophosphate, disodium pyrophosphate and mixtures thereof.

4. The dental product according to claim 1 wherein at least one of the two semi-solid flowable materials further comprise a fluoride present in an effective amount to be an anti-caries agent.

5. The dental product according to claim 1 wherein the peroxide is selected from the group consisting of hydrogen peroxide, urea peroxide, percarbonate, perphosphate, persilicate, calcium peroxide and mixtures thereof.

6. The dental product according to claim 1 wherein the semi-solid material streams each have a viscosity ranging from 20,000 to 1,500,000 centipoise at 25° C.

* * * * *